United States Patent [19]
Mano

[11] 4,229,838
[45] Oct. 28, 1980

[54] VASCULAR PROSTHESIS HAVING A COMPOSITE STRUCTURE

[75] Inventor: Hiroshi Mano, Osaka, Japan

[73] Assignee: Sumitomo Electric Industries, Ltd., Osaka, Japan

[21] Appl. No.: 921,680

[22] Filed: Jul. 3, 1978

[30] Foreign Application Priority Data

Jul. 1, 1977 [JP] Japan .................. 52/79385

[51] Int. Cl.³ .............................................. A61F 1/24
[52] U.S. Cl. ............................................. 3/1.4; 427/2
[58] Field of Search ............... 3/1.4, 1; 128/334 R; 427/2

[56] References Cited

U.S. PATENT DOCUMENTS

| 3,105,492 | 10/1963 | Jeckel | 3/1.4 X |
| 3,272,204 | 9/1966 | Artandi et al. | 3/1.4 X |
| 3,425,418 | 2/1969 | Chvapil et al. | 3/1.4 X |
| 3,511,684 | 5/1970 | Huffaker | 3/1.4 X |
| 4,082,893 | 4/1978 | Okita | 3/1 X |

FOREIGN PATENT DOCUMENTS 2508570 10/1975 Fed. Rep. of Germany ............ 3/1.4

OTHER PUBLICATIONS

"A New Vascular Prosthesis for A Small Caliber Artery", by H. Matsumoto et al., Surgery, vol. 74, No. 4, pp. 519-523, Oct. 1973.
"Expanded Polytetrafluoro-Ethylene as a Small Artery Substitute", by C. D. Campbell et al., Transactions Amer. Society for Artificial Internal Organs, vol. XX-A, 1974, pp. 86-90.

Primary Examiner—Ronald L. Frinks
Attorney, Agent, or Firm—Sughrue, Rothwell, Mion, Zinn and Macpeak

[57] ABSTRACT

A vascular prosthesis having a composite structure of a porous tubing of polytetrafluoroethylene with polyethyleneimine in the pores of the tubing, the polyethyleneimine being water-insolubilized with the amino groups quaternized and having heparin ionically bound thereto.

8 Claims, 7 Drawing Figures

VASCULAR PROSTHESIS HAVING A COMPOSITE STRUCTURE

BACKGROUND OF THE INVENTION

1. Field of the Invention

This invention relates to an antithrombic vascular prosthesis composed of polytetrafluoroethylene and quaternized polyethyleneimine having heparin bound thereto.

2. Description of the Prior Art

Fabric prostheses composed of a knitted or woven fabric of Dacron or polytetrafluorethylene in the form of a tube having inner diameters that are relatively large are now being utilized with relatively good results. In particular, good results are generally obtained with vascular prostheses for arteries which have an inner diameter of at least about 7 mm. Despite this, few small inner-diameter arteries are clinically acceptable. In venous applications, small inner-diameter prostheses exhibit a lower patency rate than in arterial applications. The rate of blood flow in veins is smaller than in arteries, and to prevent thrombosis, it is important to inhibit platelet adhesion to the inner surface of the artificial veins. This requirement is not fully met by presently available artificial veins.

Some tubings made of stretched or expanded polytetrafluoroethylene have been demonstrated to be clinically useful as vascular prostheses for arteries and veins. This is described, for example, in Soyer et al., "A New Venous Prosthesis", *Surgery*, Vol. 72, page 864 (1972), Volder et al., "A-V Shunts Created in New Ways", *Trans. Amer. Soc. Artif. Int. Organs*, Vol. 19, p. 38 (1973), Matsumoto et al., "A New Vascular Prosthesis for a Small Caliber Artery", *Surgery*, Vol. 74, p. 519 (1973), "Application of Expanded Polytetrafluoroethylene to Artificial Vessels", *Artificial Organs*, Vol. 1, p. 44 (1972), ibid., Vol. 2, p. 262 (1973), and ibid., Vol. 3, p. 337 (1974), Fujiwara et al., "Use of Goretex Grafts for Replacement of the Superior and Inferior Venae Cavae", *The Journal of Thoracic and Cardiovascular Surgery*, Vol. 67, p. 774 (1974), and Belgian Pat. No. 517,415.

The results of these clinical experiments are summarized below.

When a suitable porous prosthesis is implanted as a conduit within the arterial system, the fine pores are clogged by clotted blood, and the inside of the prosthesis is covered with a clotted blood layer. The clotted blood layer is made up of fibrin, and the thickness of the fibrin varies, for example, according to the material of and the surface structure of the prosthesis. Since the thickness of the fibrin approaches 0.5 to 1 mm when a knitted or woven fabric of Dacron or polytetrafluoroethylene is used as the prosthesis, success is achieved only with those blood vessels which are not occluded due to this increase in wall thickness by the fibrin layer (that is, arteries having an inside diameter of 5 to 6 mm or more). Generally, knitted or woven prostheses having smaller inner diameters have not been successful.

A polytetrafluoroethylene tubing which has been stretched has a microstructure composed of very fine fibers and nodes connected together by the fibers. The diameters of the fibers vary depending on various stretching conditions, and can be made much smaller than fibers of the knitted and woven fabrics mentioned above.

It has been confirmed clinically that when a structure composed of fibers and nodes is expressed in terms of pore sizes and porosities, or fiber lengths and nodular sizes, a polytetrafluoroethylene tubing having a pore size of from about $2\mu$ to about $30\mu$ (pore sizes below about $2\mu$ are undesirable), a porosity of about 78% to about 92%, a fiber length of not more than about $34\mu$ (fiber lengths of about $40\mu$ to about $110\mu$ are undesirable), a nodular size of not more than about $20\mu$, and a wall thickness of about 0.3 mm to about 1 mm exhibits a high patency rate without substantial occlusion by fibrin deposition.

It has been reported, however, that venous prostheses exhibit a much lower patency rate than arterial prostheses, and do not prove to be entirely satisfactory for prosthetic purposes. It has also been reported that when a vascular prosthesis has too high a porosity, a tearing of the prosthesis by the suture used in joining the prosthesis with the vessel of the patient tends to occur.

In the healing process after implantation, connective tissue first develops on the outer periphery of the polytetrafluoroethylene tubing and the tissue organizes, and afterwards the fibrin layer on the inner surface of the tubing organizes. At this time, a continuity of the intimas of the host's vessels with the neointima of the inner surface of the vascular prosthesis is established, and simultaneously, the fibrin layer is replaced by the fibrous tissue which has entered the prosthesis through the fine pores from the periphery of the prosthesis. Furthermore, after a certain period of time, the neointimas at the inner surface are connected firmly to the connective tissue lining the outer wall of the prosthesis, thereby completing the formation of an artery. It is known that this artery formation requires a period of usually about 4 to 6 months. It is known on the other hand that with vascular prostheses implanted in veins, the rate of entry of the connective tissue from the periphery thereof is slower than for arterial implantation.

However, despite these reported clinical results, reproducible, good results have not been obtained. A porous tubing of polytetrafluoroethylene permits the adsorption of plasma protein. Platelets adhere to the adsorbed plasma protein to form fibrin fibers which capture blood corpuscles and become a fibrin deposited layer. This deposited layer is expected to subsequently form a pseudointima of the prosthesis. However, the fibrin deposited layer is frequently too thick, and insufficient nutrition of the pseudointima or neointima occurs. This will result in disconnection by necrosis or in thrombic occlusion of the inner surface of the prosthesis.

SUMMARY OF THE INVENTION

An object of this invention is to provide a vascular prosthesis having a composite structure composed of a porous tubing of polytetrafluoroethylene and water-insolubilized and quaternized polyethyleneimine having heparin ionically bound thereto, with the polyethyleneimine being provided in the pores of the porous tubing. Functionally, the surface of the prosthesis is rendered hydrophobic and is simultaneously charged negatively by the polytetrafluoroethylene having a low surface energy whereby antithrombic character is achieved. Polyethyleneimine which is water-insolubilized and quaternized and has heparin ionically bound thereto is provided in the pores of the porous tubing of polytetrafluoroethylene, and consequently, a film of water molecules strongly bound thereto is formed. This prevents the adsorption of plasma protein which becomes a trigger for fibrin deposition. Furthermore, in conjunction with the anticoagulating action of the heparin, antithrombic characteristics are achieved.

Another object of this invention is to provide a vascular prosthesis of a stretched polytetrafluoroethylene tubing in which the pore size of the outer surface is larger than that of the inner surface thereby to increase the rate of entry of the connective tissue from the outer periphery of the prosthesis. The smaller size of the pores of the inner surface is believed to reduce the surface stasis of blood flow. Platelet adhesion is reduced by providing water-insolubilized and quaternized polyethyleneimine having heparin ionically bound thereto in the pores of the polytetrafluoroethylene tubing. As a result, the amount of thrombus formation at the inner surface decreases, and the fibrin layer becomes extremely thin. Thus, the neointima on the inner surface is thinner than in a similarly dimensioned prior art vascular prosthesis.

Still another object of this invention is to provide a vascular prosthesis of a stretched polytetrafluoroethylene tubing in which the pore size of the outer surface is larger than that of the inner surface, thereby allowing the connective tissue from the outer periphery of the prosthesis to grow and develop fully, and consequently supplying sufficient nutrient to the neointima formed at the inner surface to prevent calcification in the prosthesis wall that may otherwise occur due to degenerative change with the lapse of time, thus increasing the patency rate of the prosthesis after implantation.

According to this invention, a microstructure composed of fibers and nodes which is obtained by stretching a tubing of polytetrafluoroethylene in at least one axial direction and heating the stretched tubing to at least about 327° C. is used as one starting material. Then, the pores of the microstructure are filed with a solution of polyethyleneimine, and the polyethyleneimine is subjected to a water-insolubilization treatment and a quaternization treatment. Then, heparin is ionically bound to the polyethyleneimine to form a composite structure. Thus, the invention provides a vascular prosthesis having a high rate of patency which permits a thin neointima to form on the inner surface of the prosthesis after implantation with sufficient nutrition being provided the neointima thereby to retain the neointima without degenerative change and without occlusion of the interior cavity of the prosthesis.

BRIEF DESCRIPTION OF THE ACCOMPANYING DRAWINGS

FIG. 1 is a schematic cross-section of a composite structure vascular prosthesis in accordance with the present invention wherein 1 represents a porous polytetrafluoroethylene tube having an outer sidewall 10 and an inner sidewall 11 where pores 12 are shown filled with polyethyleneimine material 13. Like numerals are used in FIGS. 2–6 to represent like elements.

FIG. 2 is an embodiment of the present invention similar to FIG. 1 except the composite structure vascular prosthesis has nodes 14 connected to one another by fibers 15, where the microstructure of outer sidewall 10 and inner sidewall 11 is different.

FIG. 3 is an embodiment of the present invention similar to FIG. 2 except that the diameter of the fibers 15a at the outer sidewall 10 is at least two times the diameter of the fibers 15b at the inner sidewall 11.

FIG. 4 is an embodiment of the present invention similar to FIG. 2 except that the directions of the fibers 15c at the inner sidewall 11 are distributed more radially than the directions of the fibers 15d at the outer sidewall 10.

FIG. 5 is an embodiment of the present invention similar to FIG. 2 but the long axis of each node 14a at the outer sidewall 10 is at least two times the long axis of each node 14b at the inner sidewall 11.

FIG. 6 is an embodiment of the present invention similar to FIG. 2 but the size of the pores 12a at the outer sidewall 10 is larger than the size of the pores 12b at the inner sidewall 11.

FIG. 7 is an embodiment of the present invention similar to FIG. 1 but polyethyleneimine 13 is present only in the pores 12c at the inner surface side.

DETAILED DESCRIPTION OF THE INVENTION

Figure 1:
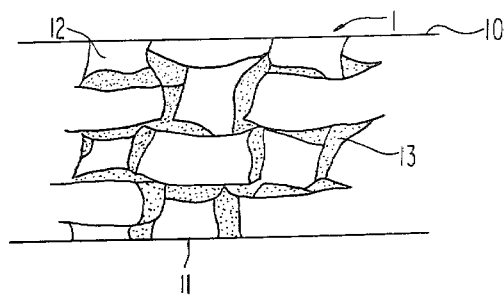
Figure 2:
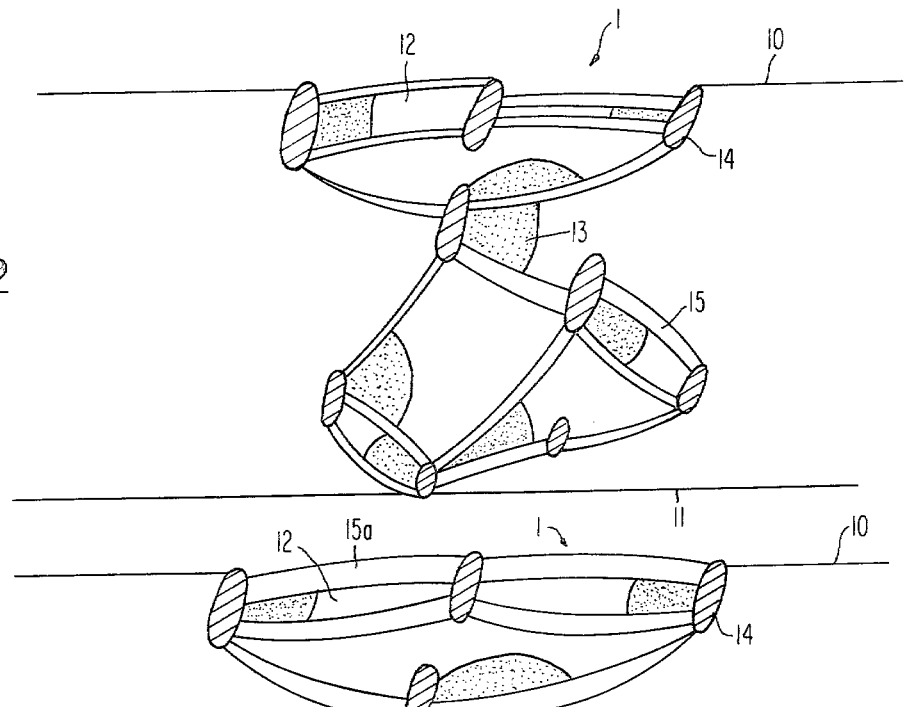
Figure 3:
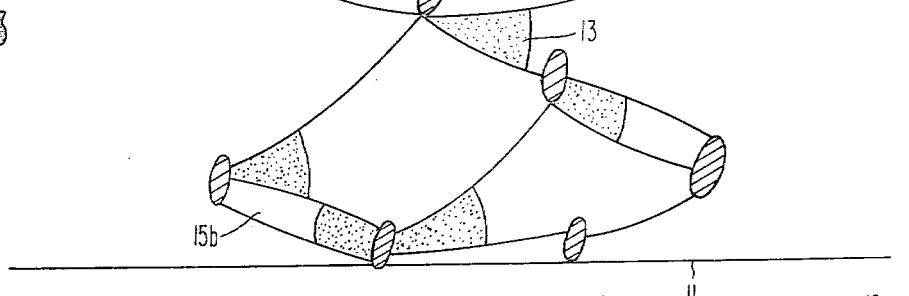
Figure 4:
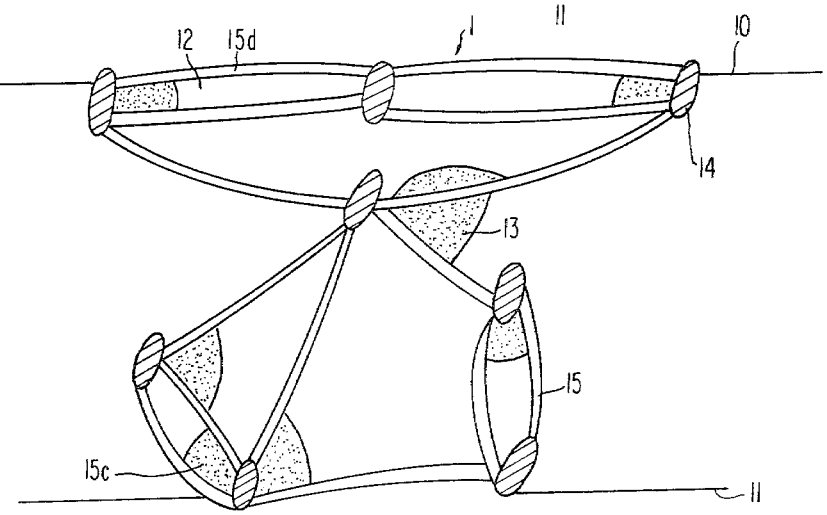
Figure 5:
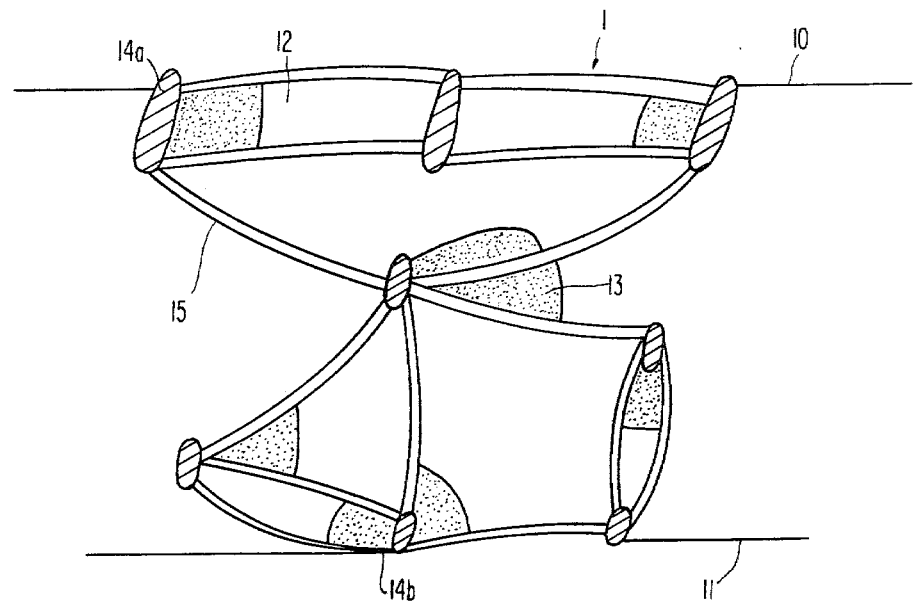
Figure 6:
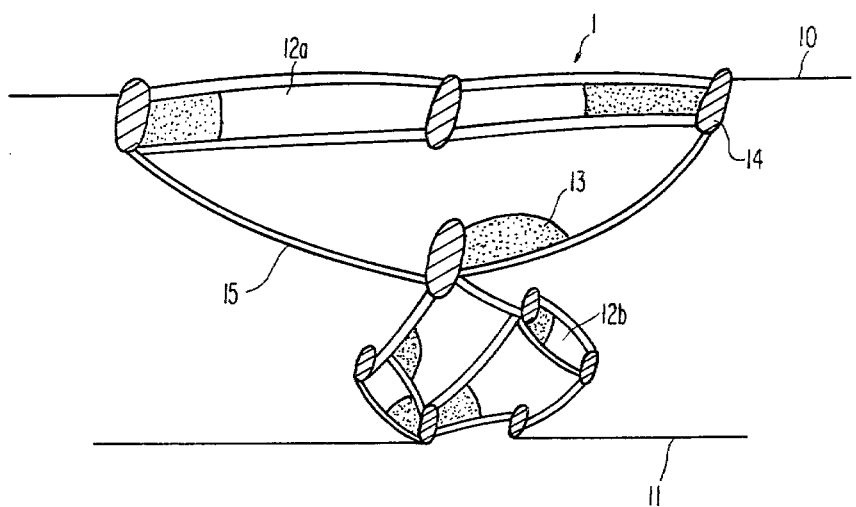
Figure 7:
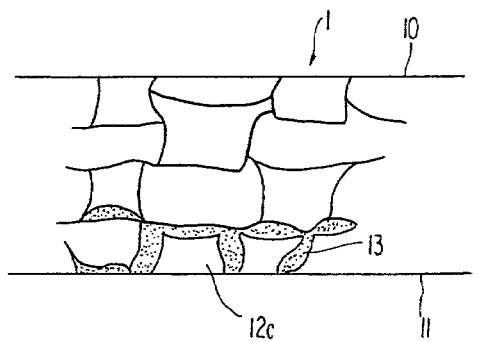

In order to stretch and sinter tubings of polytetrafluoroethylene, the methods described in Japanese Patent Publications No. 13560/67 and U.S. Pat. Nos. 3,953,566 and 3,962,153 can basically be utilized. First, a liquid lubricant is mixed with a sintered powder of polytetrafluoroethylene, and the mixture is extruded into a tubular form by a ram-type extruder. The tubing is stretched at least monoaxially while the tubing is heated at a temperature of less than about 327° C., the polytetrafluoroethylene sintering temperature. Then, while the tubing is fixed so that it does not shrink, the tubing is heated to a temperature of at least about 327° C. to set the stretched and expanded structure and to form a tubing having increased strength.

Any polytetrafluoroethylenes, e.g., homopolymers, which are commercially available can be used in this invention with those having a molecular weight ranging from about $1 \times 10^6$ to about $9 \times 10^7$ being preferred.

Polyethyleneimine, another starting material, is used to bind heparin to the polytetrafluoroethylene tubing to render the tubing antithrombic and form a hydrophilic film. A suitable molecular weight range for the polyethyleneimine which can be used in this invention is about $1 \times 10^4$ to about $9 \times 10^5$. Any commercial grades of polyethyleneimine can be used for this purpose. Commercially available polyethyleneimines are obtained by the polymerization of ethyleneimine. Usually, they are not linear high-molecular-weight polymers, but have a branched structure containing primary, secondary or tertiary amine groups. Polyethyleneimine of such a structure suffices for the purposes of the present invention, and the polyethyleneimine may also contain a substituent. In short, polyethyleneimines of any structure can be utilized in the present invention. Since, commercially available grades can be used, their quality is constant for example in regard to the degree of polymerization. In actually impregnating or coating a solution of polyethyleneimine in and on a porous tubing of polytetrafluoroethylene, the concentration of the polyethyleneimine and the method of insolubilization are selected depending on the porosity, pore size, etc. of the porous tubing. In general, the polyethyleneimine can be employed in a concentration of above 0.1 to about 30% by weight.

Water is suitable as a solvent for the polyethyleneimine. When the pore size of the polytetrafluoroethylene tubing is small, the pores of the polytetrafluoroethylene tubing cannot be directly filled with an aqueous solution of polyethyleneimine. For this reason, the tubing is first immersed in a liquid which is soluble in water and having a low surface tension, such as methanol, ethanol, acetone and an aqueous solution of a surface active agent, and then in water to replace the liquid in the pores of the tubing with water. The tubing is then immersed in an aqueous solution of polyethyleneimine, preferably at a polyethyleneimine concentration to about 0.1 to about 20% by weight. Since polyethyleneimine is also soluble in a lower alcohol such as methanol, ethanol or ethylene glycol, the polyethyleneimine may be dissolved in such a solvent and the porous tubing can be impregnated directly with such a solution.

In order to uniformly impregnate the pores of the porous tubing with the aqueous solution of polyethyleneimine, a sufficient period of time for the diffusion of the polyethyleneimine to occur is allowed to elapse after the immersion before the subsequent insolubilization reaction step is performed. In general, a sufficient period of time for the diffusion has been found to be about 0.1 to about 20 hours. Another method for distributing the polyethyleneimine uniformly in the pores of the tubing is to repeat the steps of immersion of the porous tubing in the polyethyleneimine solution and drying the tubing. It has been ascertained that by again contacting the porous tubing, which has been impregnated with the polyethyleneimine solution and then dried (e.g., at from room temperature (10°–25° C.) to about 100° C., preferably up to 80° C.) with the polyethyleneimine solution, the solution readily penetrates into the interior of the pores, and the polyethyleneimine concentration in the interior spaces of the pores roughly doubles. For repeat impregnation, drying between impregnations is desirable but not essential. Vacuum impregnation or pressure impregnation may be utilized, if desired. In particular, the pores can be effectively impregnated with the polyethyleneimine solution from the inner cavity of the porous tubing by applying pressure to the solution.

In the next step, a chemical reaction to render the polyethyleneimine water-insoluble is carried out. This chemical reaction is not particularly critical so long as the polyethyleneimine is rendered water-insoluble. The type of the reaction can be chosen freely also in view of the fact that the material constituting the porous tubing is polytetrafluoroethylene which has very good chemical resistance and thermal stability.

Polyethyleneimine is a very readily water-soluble polymer. Water-insolubilization can be achieved by cross-linking the polyethyleneimine into a network structure. Reaction of the polyethyleneimine with an aldehyde such as formaldehyde or glyoxal is a typical example of the crosslinking process. If the reaction takes place in a single molecule of polyethyleneimine, the linear molecule changes to a cyclic molecule. If the reaction takes place between two molecules of polyethyleneimine, the molecules change to starlike molecules or macrocyclic molecules. When the crosslinking reaction further proceeds and involves many molecules, a three-dimensional crosslinked network structure will result. As the degree of polymerization of polyethyleneimine increases, the water-insolubilization of the polyethyleneimine can be advantageously achieved with fewer crosslinking reactions. Furthermore, the swellability of polyethyleneimine with water becomes greater. Examples of compounds which react with polyethyleneimine and act as crosslinking agents include ketones, carboxylic acids, acid anhydrides, acyl halides, isocyanic acid esters, isothiocyanic acid esters, and epoxides in addition to the aldehydes. Reactions with these compounds, with carbonyl group containing compounds being preferred, can be utilized for water-insolubilization.

The water-swellability, or the water content, of the polyethyleneimine after water insolubilization varies greatly according to the reaction procedure for water insolubilization and the reaction conditions used. Hence, these factors may be selected depending or the intended end-use purpose. When a suitable reaction procedure and suitable reaction conditions are selected, a porous composite structure can also be obtained which consists of a tubing of polytetrafluoroethylene and a microporous swollen gel-like product of polyethyleneimine impregnated in the pores of the tubing. It is surprising to note that by varying the factors, described above the pore size of the microporous swollen gel changes from $10\mu$ to $0.01\mu$ or even to $0.001\mu$. Thus, the adsorption of plasma protein can be reduced, and the surface of the interior cavity of the tubing can be made smooth to an extent that the stream of the blood flow is not disturbed.

Following the water-insolubilization reaction, a quaternization reaction is carried out. The water-insolubilized polyethyleneimine is converted by quaternization into a compound having a quaternary ammonium salt type cation as a fixed ion. A typical example of a reaction for this purpose is the reaction of the water-insolubilized polyethyleneimine with an alkyl halide. Use of an excess amount of the alkyl halide is preferred in order to assure complete quaternization. Examples of suitable alkyl halides which can be used are ethyl chloride, butyl chloride, allyl chloride, benzyl chloride, ethyl bromide, propyl bromide, butyl bromide, methyl iodide, and ethyl iodide. A similar reaction can be carried out by using alkyl sulfates or alkyl sulfonates corresponding to these halides described above.

The product is then subjected to a treatment to ionically bind heparin to the fixed cation generated as a result of the quaternization. Heparin is known to be an anticoagulant for blood. According to this invention, a vascular prosthesis having antithrombic properties can be obtained by ionically binding heparin to the fixed cation. To achieve this, the product is immersed in an aqueous solution of heparin at room temperature (e.g., 10°–25° C.) to a temperature of not more than about 100° C. for 1 hour to several days. A suitable concentration of heparin which can be employed in this invention is about 100 to about 10,000 units/ml. The heparin solution may also be an aqueous solution of a suitable concentration of commercially available sodium heparin.

Coating or mixing of heparin on or with a material to be used for medical treatment is also practiced to achieve anti-thrombic characteristics. However, this method has the defect that heparin easily comes off from the material. A method involving covalently bonding heparin to the material is also practiced, but has not given good anti-thrombic properties. In view of this, ionic bonding of heparin in accordance with this invention is believed to be most effective for imparting anti-thrombic properties.

Polyethyleneimine water-insolubilized and quaternized and having heparin ionically bound thereto may be provided only partially in the pores of the porous polytetrafluoroethylene tubing. Particularly, in a preferred embodiment, a vascular prosthesis of a porous polytetrafluoroethylene tubing in which heparin-bound polyethyleneimine is provided only in those pores which are on the inner surface of the tubing reduces blood leakage after implantation, and the interior cavity of the prosthesis is not occluded because of the antithrombic property of the inner surface of the tubing. Such a prosthesis exhibits a high patency rate even in application to small-caliber vessels in which the patency rate has in the past been regarded as extremely low. In order to provide water-insolubilized and quaternized polyethyleneimine having heparin ionically bound thereto in those pores which are on the inner surface side of the porous tubing, the polyethyleneimine solution can be impregnated only from the inner surface of the porous tubing, and the subsequent water-insolubilization reaction should be started only at the inner surface. The reaction should be terminated by washing the product with water after an appropriate period of time before the reaction reaches the outer surface of the tubing.

In another preferred embodiment of the invention, a polytetrafluoroethylene tubing whose outer surface and inner surface have different micro-fibrous structures is used as a starting material. The micro-fibrous structure comprises fibers and nodes connected to one another by the fibers. Such a starting material desirably has a micro-fibrous structure in which the average fiber size of the outer surface is at least two times the average fiber size of the inner surface.

Another preferred micro-fibrous structure is one in which the fiber direction of the inner surface is more radially distributed than the fiber direction of the outer surface, or the long axes of the nodes at the outer surface are at least two times longer than those of the nodes at the inner surface.

In these micro-fibrous structures, the inner surface is finer and smoother than the outer surface. Consequently, the rate of entry of the connective tissues from the outer periphery after implantation increases and the surface stasis of the blood flow on the inner surface is reduced. Furthermore, platelet adhesion can be reduced by providing water-insolubilized and quaternized polyethyleneimine having heparin ionically bound thereto in the pores of the micro-fibrous structure.

A structure of these types can be obtained by sintering the stretched tubing at a temperature of at least about 327° C. while forcibly cooling the inner surface of the tubing and starting the heating at the outer periphery of the tubing.

The temperature is so adjusted that the resin portion of the inner surface of the tubing is at a temperature of at least about 327° C., the sintering temperature, while continuously exposing the inner surface of the tubing to a cooling medium such as air by continuously introducing the cooling medium into the interior cavity of the tubing, or continuously reducing the pressure of the interior cavity of the tubing.

As a result, the resin fibers at the outside surface of the tubing are exposed for a long time to a temperature of at least about 327° C., and two or more fibers at the outer surface originally having the same fibrous structure (especially the same size) as the inner surface coalesce and gradually become thicker. For example, when the fiber diameter doubles four fibers are fused and coalesced.

The thickness of the inner surface structural portion of the tubing and the thickness of the outer surface structural portion of the tubing are varied by changing the amount of the cooling medium passed through the interior cavity of the tubing and the amount of heat supplied externally. When the amount of the cooling medium is decreased, and the amount of heat supplied externally is increased, the thickness of the outer surface structural portion increases. Increasing the amount of the cooling medium results in an increase in the thickness of the inside surface structural portion. Since in this case also, the size of the nodular portion does not change, the nodular dimension of the outer surface is approximately equal to that of the inner surface.

When the tubing is stretched lengthwise and then expanded in the radial direction, the micro-fibrous structure of fibers and nodes changes abruptly. The nodes of a tubing which has been stretched only in the longitudinal direction have a shape approximating an ellipsoid and have a relatively uniform size. However, with a tubing which has been stretched in the longitudinal direction and then expanded in the radial direction, the nodes generated in the longitudinal direction divide into smaller portions depending on the extent of expansion, and fibers form again among the nodes. The shape of the nodes or the length, direction and size of the fibers will vary depending on the stretch ratios in the longitudinal direction and the radial direction. At any rate, it is to be noted that the shape of the nodes, the length, the size, etc. of the fibers change depending on the extent of expansion in the radial direction from the shape, length, size, etc. attained by stretching the tubing only in the longitudinal direction.

The most preferred embodiment comprises stretching the tubing first in the longitudinal direction and then expanding the tubing in the radial direction. By heating the outer surface of the tubing to at least about 327° C., the crystalline melting point of polytetrafluoroethylene, but maintaining the inner surface of the tubing at below 327° C. prior to expansion in the radial direction, a composite structure can be produced in which the outer surface of the tubing has a micro-fibrous structure formed by stretching only in the longitudinal direction and the inner surface of the tubing has a biaxially stretched micro-fibrous structure formed by stretching also in the radial direction. Needless to say, it is possible to change the micro-fibrous structures of the outer and inner surfaces of the tubing by first expanding the tubing in the radial direction and then stretching the tubing in the longitudinal direction.

A more detailed description of the polytetrafluoroethylene tubings and their characteristics which can be used in this invention appear in copending applications Ser. No. 760,789, filed Jan. 19, 1977, now abandoned, and Ser. No. 825,513, filed Aug. 17, 1977.

Water-insolubilized and quaternized polyethyleneimine having heparin ionically bound thereto can be provided in the pores of such a polytetrafluoroethylene tubing by the procedure described hereinabove.

The fibrous structure at the outer surface of the tubing is less dense than that at the inner surface, and this produces various effects as described below.

Firstly, this serves to increase the mechanical strength of vascular prostheses made of such a tubing preventing the prosthesis from being torn in the longitudinal direction by the suture during implantation. It is possible for only the inner surface fibrous structure of the tubing to act as a bag-like receptacle for transporting blood. For application to arteries, however, the tubing must withstand a blood pressure of about 120 mmHg, and should not be compressed by elastic fibroblasts that develop on the outer periphery thereof. In addition, the tubing must withstand suturing at the time of surgery. The force required to cut the fibers can be increased by increasing the diameters of the fibers at the outer surface of the tubing, and increasing the number of fibers that are aligned at right angles to the direction of possible tearing. In particular, a tubing that has been stretched and then expanded to increase the fiber diameter has improved tear strength.

Secondly, as a result of decreasing the dimension of the fibrous structure at the inner surface of the vascular prosthesis made of the polytetrafluoroethylene tubing, the surface resistance of the tubing blood flow is reduced, and consequently, platelet adhesion is reduced. Platelets which have contacted the surface of the prosthesis and adhered thereto aggregate with each other reversibly in the presence of adenosine diphosphate and calcium ion, after which they adhere irreversibly and form a thrombus together with fibrin. The thrombus layer becomes thinner as the amount of platelets that have adhered decreases. The thickness of the initial thrombus layer increases as the fibrin deposits onto it, and this finally causes occlusion. Therefore, in order to obtain vascular prostheses free from occlusion, it is essential to decrease the thickness of the initial thrombus layer. This necessity is more pronounced in veins than in arteries. In other words, a reduction in the thickness of neointimas on the inner surface of the prostheses can be expected.

As a third effect, fibroblasts rapidly enter the prosthesis from the outer periphery of the prosthesis and grow fully as a result of an increase in the size of the openings in the outer surface fibrous structure of the prosthesis. It is already known that fibroblasts readily enter a vascular prosthesis made of a knitted or woven fabric of Dacron, or polytetrafluoroethylene, etc., because such a prosthesis has a tubular wall of a loose structure. However, bleeding occurs through the wall immediately after implantation, and results in an increase in the thickness of the fibrin layer on the inner surface of the prosthesis. Further increase leads to calcification and occlusion. In a prosthesis made of polytetrafluoroethylene having the same fibrous structures both at the outer and inner surfaces, it is essential to decrease the thickness of the fibrin layer that results from platelet adhesion by making the pore size sufficiently small to prevent bleeding, and therefore, the ease of entry of fibroblasts from the outer periphery of the prosthesis must be sacrificed to some extent.

When the fiber diameter of the outer surface of the prosthesis of this invention is at least two times larger than the fiber diameter of the inner surface, it is possible to reduce the thickness of the fibrin layer at the inner surface of the prothesis and facilitate entry of fibroblasts from the periphery. Furthermore, nutrient supply to the neointimas formed at the inner surface of the prosthesis can be effected sufficiently through capillaries which densely develop on fully grown fibroblasts. It is possible therefore to greatly reduce calcification of the neointimas that may result from nutritional deficiency.

In arterial prostheses, nutrition can be effected not only through capillaries at the fibroblasts, but also from the blood within the cavity of the prostheses. However, in venous prostheses, nutrition from the blood can hardly be expected, and must rely exclusively upon the capillaries present on the fibroblasts that have come through the outer periphery. Accordingly, the entry of fibroblasts from the outer periphery of vascular prostheses is important not only for the formation of neointimas, but also for preventing calcification of the neointimas which may occur due to nutritional deficiency after implantation and thereby for increasing the patency rate of the prosthesis after operation. This is more important in venous prostheses.

Vascular prostheses must have pore sizes which are small enough to keep the blood during circulation from leaking through the tubular wall, and which are large enough to permit entry of fibroblasts from the outer periphery without obstruction. With the prosthesis of this invention, this requirement can be met not only by the porosity (e.g., of about 78% to about 92%), fiber length (e.g., of not more than about $34\mu$) and pore size (e.g., of about $2\mu$ to about $30\mu$) of the polytetrafluoroethylene tubing, but also by the condition of water-insolubilized and quaternized polyethyleneimine having heparin ionically bound thereto which is provided in the pores of the tubing.

A polytetrafluoroethylene tubing used as a conventional prosthesis from which leakage of the circulating blood through the wall of the prosthesis occurs because of high porosity, etc. can also have blood leakage prevented by completely filling a microporous swollen gel of water-insolubilized and quaternized polyethyleneimine having heparin ionically bound thereto in the pores of the tubing. Fibroblasts from the outer periphery of the prosthesis can successively enter the filled polyethyleneimine and thus grow.

The effect of providing the water-insolubilized and quaternized polyethyleneimine having heparin ionically bound thereto in a polytetrafluoroethylene tubing having porosity characteristics within the ranges feasible heretofore as vascular prostheses is that at the time of contact with the blood, the water of adsorption of the polyethyleneimine inhibits the adsorption of plasma protein, and thus it is difficult for a fibrin layer to form. In conjunction with the anti-clotting action of heparin, this effect provides the vascular prosthesis with antithrombic properties.

The composite vascular prosthesis of the invention composed of a porous tubing of polytetrafluoroethylene and water-insolubilized and quaternized polyethyleneimine having heparin ionically bound provided in the pores, especially in those pores which are on the inner surface side, results in little vascular occlusion by the increased thickness of the fibrin layer after surgical operation occurring, expedites the healing of the patients, and prevents the degenerative change of the neointimas formed. Accordingly, the prostheses in accordance with this invention contribute greatly not only to surgery but also to industry.

The following Examples are given to illustrate the present invention more specifically. It should be understood however that the present invention is not to be construed as being limited by these examples.

In these examples, the bubble point is the pressure at which the first air bubble passes through the porous tubing when a pneumatic pressure is applied to the inner surface of the tubing immersed in isopropyl alcohol. Unless otherwise indicated herein, all parts, percents, ratios and the like are by weight.

EXAMPLE 1

A commercially available 30% aqueous solution of polyethyleneimine (mol. wt.: about 40,000) was diluted with isopropyl alcohol to prepare a 2% solution. The solution was forced into a porous polytetrafluoroethylene tubing from the inner surface of the tubing. The porous tubing had been prepared from polytetrafluoroethylene by stretching and sintering and had an inside diameter of 4.3 mm, a thickness of 0.40 mm, a bubble point of 0.25 kg/cm² and a porosity of 80%. The porous tubing was air dried at 20° C. for 2 minutes, and then immersed for 2 minutes in a 4% aqueous solution of glyoxal to render the polyethyleneimine water-insoluble. The tubing was washed with water, dried, and then immersed in a 50% ethanol solution of methyl iodide at 20° C. for 3 hours to quaternize the polyethyleneimine. The tubing was washed with water, and heated at 90° C. for 30 minutes in distilled water to remove unreacted material. Furthermore, the tubing was washed with a 1% aqueous solution of sodium chloride, dried, and impregnated with an aqueous solution of heparin sodium in a concentration of 1000 units/ml to bind the heparin. Two hours later, a part of the tubing was taken as a sample. The sample was washed with water, and then contacted with a solution of toluidine blue indicator, whereupon it assumed a reddish violet color. Thus, the bonding of heparin was confirmed. The resulting tubing had a bubble point of 0.29 kg/cm².

EXAMPLE 2

A commercially available 30% aqueous solution of polyethyleneimine (mol. wt.: about 50,000) was diluted with isopropyl alcohol to prepare a 7% solution. The solution was forced into the same type of porous polytetrafluoroethylene tubing as described in Example 1 from the inner surface of the tubing, dried in air at 20° C. for 2 minutes, and immersed for 2 1 minutes in a 5% aqueous solution of glyoxal to render the polyethyleneimine water-insoluble. In the same manner as in Example 1, the tubing was subjected to a quaternization reaction and a heparin-binding treatment. The bonding of heparin was confirmed in the same manner as in Example 1. The resulting tubing had a bubble point of 0.44 kg/cm².

While the invention has been described in detail and with reference to specific embodiments thereof, it will be apparent to one skilled in the art that various changes and modifications can be made therein without departing from the spirit and scope thereof.

What is claimed is:

1. A vascular prosthesis having a composite structure of a porous tubing of polytetrafluoroethylene with polyethyleneimine in the pores of the tubing, said polyethyleneimine being water-insolubilized with the amino groups quaternized and having heparin ionically bound thereto.

2. The vascular prosthesis of claim 1 wherein the polyethyleneimine is a microporous polyethyleneimine which is water-insolubilized with the amino groups quaternized and has heparin ionically bound thereto.

3. The vascular prosthesis of claim 1 wherein the polytetrafluoroethylene has a microstructure composed of fibers and nodes connected to one another by the fibers, and the microstructure of the outer surface of the tubing differs from the microstructure of the inner surface of the tubing.

4. The vascular prosthesis of claim 3, wherein the outer surface of the porous tubing has an average fiber diameter at least two times larger than the average fiber diameter of the inner surface of the porous tubing.

5. The vascular prosthesis of claim 3, wherein the direction of the fiber alignment of the inner surface of the porous tubing is more radially distributed than the direction of the fiber alignment of the outer surface of the porous tubing.

6. The vascular prosthesis of claim 3, wherein the long axes of the nodes at the outer surface of the porous tubing are at least two times longer than the long axes of the nodes at the inner surface of the porous tubing.

7. The vascular prosthesis of claim 3, wherein the pore diameter of the outer surface of the porous tubing is larger than the pore diameter of the inner surface of the porous tubing.

8. The vascular prosthesis of claim 1, wherein said polyethyleneimine is present only in those pores of the porous tubing which are on the inner surface of the porous tubing.

* * * * *